(12) United States Patent
Pereira et al.

(10) Patent No.: US 11,623,090 B2
(45) Date of Patent: Apr. 11, 2023

(54) DEEP BRAIN STIMULATION METHOD

(71) Applicant: ST GEORGE'S HOSPITAL MEDICAL SCHOOL, London (GB)

(72) Inventors: Erlick Pereira, London (GB); Francesca Morgante, London (GB)

(73) Assignee: ST GEORGE'S HOSPITAL MEDICAL SCHOOL, London (GB)

( * ) Notice: Subject to any disclaimer, the term of this patent is extended or adjusted under 35 U.S.C. 154(b) by 0 days.

(21) Appl. No.: 17/350,057

(22) Filed: Jun. 17, 2021

(65) Prior Publication Data

US 2021/0393959 A1  Dec. 23, 2021

(30) Foreign Application Priority Data

Jun. 17, 2020 (GB) .................................. 2009230

(51) Int. Cl.
*A61N 1/36* (2006.01)
*A61N 1/05* (2006.01)

(52) U.S. Cl.
CPC ....... *A61N 1/36067* (2013.01); *A61N 1/0534* (2013.01); *A61N 1/36171* (2013.01); *A61N 1/36175* (2013.01)

(58) Field of Classification Search
CPC .............. A61N 1/36067; A61N 1/0534; A61N 1/36171; A61N 1/36175
See application file for complete search history.

(56) References Cited

U.S. PATENT DOCUMENTS

| | | | | |
|---|---|---|---|---|
| 2012/0053658 | A1* | 3/2012 | Gabriela | A61N 1/0534 607/62 |
| 2013/0218232 | A1* | 8/2013 | Giftakis | A61N 1/36146 607/45 |
| 2017/0072198 | A1* | 3/2017 | Makous | A61N 1/0534 |
| 2017/0360354 | A1* | 12/2017 | Montgomery | A61B 5/02042 |

OTHER PUBLICATIONS

Avanzino, Laura et al., "How Does the Cerebellum Contribute to the Pathophysiology of Dystonia?," Basal Ganglia 2012; 2(4): pp. 231-235.
Bain, P G et al., "Assessing Tremor Severity," Journal of Neurology, Neurosurgery, and Psychiatry, 1993; 56(8), pp. 868-873.
Boston Scientific, "Vercise™ Deep Brain Stimulator System," https://www.bostonscientific.com/en-EU/products/deep-brain-stimilationsystems/vercise-deep-brain-stimulation-system.html, web site pages, printed out on Sep. 15, 2021 (origination date unknown), 3 pp.

(Continued)

*Primary Examiner* — Michael W Kahelin
(74) *Attorney, Agent, or Firm* — Nixon & Vanderhye P.C.

(57) ABSTRACT

The disclosure concerns a method for the treatment of cervical dystonia, comprising inserting a stimulation device into the brain of a patient, the stimulation device being configured to provide electrical stimulation to affect first and second stimulation targets within the brain. The first stimulation target is the subthalamic nucleus (STN); and the second stimulation target is the ventral intermediate nucleus (VIM), or the ventralis oralis posterior thalamus (VOP), or both the ventral intermediate nucleus (VIM) and the ventralis oralis posterior thalamus (VOP).

17 Claims, 7 Drawing Sheets
(1 of 7 Drawing Sheet(s) Filed in Color)

(56) References Cited

OTHER PUBLICATIONS

Burke, Robert E. et al., "Validity and Reliability of a Rating Scale for the Primary Torsion Dystonias," Neurology, Jan. 1985;35(1), pp. 73-77.
Chung, Moonyoung et al., "Different Clinical Course of Pallidal Deep Brain Stimulation for Phasic- and Tonic-Type Cervical Dystonia," Acta Neurochir (2016) 158(1), pp. 171-180.
Comella, Cynthia L. et al., "Development of the Comprehensive Cervical Dystonia Rating Scale: Methodology.," Movement Disorders Clinical Practice, vol. 2, No. 2, 2015, 13 pp.
Foote, Kelly D., MD et al., "Dual Electrode Thalamic Deep Brain Stimulation for the Treatment of Posttraumatic and Multiple Sclerosis Tremor," Operative Neurosurgery, vol. 58, Apr. 2006, pp. ONS-280-ONS-286.
Kleiner-Fisman, Galit, M.D. et al., "Subthalamic Nucleus Deep Brain Stimulation for Severe Idiopathic Dystonia: Impact on Severity, Neuropsychological Status, and Quality of Life," J Neurosurg, vol. 107, Jul. 2007, pp. 29-36.
Krack, Paul et al., "From Off-Period Dystonia to Peak-Dose Chorea. The Clinical Spectrum of Varying Subthalamic Nucleus Activity," Brain 1999; 122 (Pt 6), pp. 1133-1146.
Kuncel, Alexis M., PhD et al., "Myoclonus and Tremor Response to Thalamic Deep Brain Stimulation Parameters in a Patient with Inherited Myoclonus-Dystonia Syndrome," Clin Neurol Neurosurg, 111(3), Apr. 2009, 7 pp.
Morishita, Takashi et al., "Should We Consider Vim Thalamic Deep Brain Stimulation for Select Cases of Severe Refractory Dystonic Tremor," Stereotactic and Functional Neurosurgery; 88(2), Fpp. 98-104.
Müller, J. et al, "Craniocervical Dystonia Questionnaire (CDQ-24): Development and Validation of a Disease-Specific Quality of Life Instrument," J Neurol Neurosurg Psychiatry 2004; 75(5), pp. 749-753.
Neudorfer, Clemens, MD et al., "Combined Deep Brain Stimulation of Subthalamic Nucleus and Ventral Intermediate Thalamic Nucleus in Tremor-Dominant Parkinson's Disease Using a Parietal Approach," Neuromodulation Jun. 2019;22(4), 10 pp.
Ostrem, J. L., MD et al., "Subthalamic Nucleus Deep Brain Stimulation in Primary Cervical Dystonia," Neurology 2011; 76(10), pp. 870-878.
Ostrem, Jill L., MD et al., "Subthalamic Nucleus Deep Brain Stimulation in Isolated Dystonia, A 3-Year Follow-Up Study" Neurology 2017; 88(1), 12 pp.
Pauls, K. Amande M., MD, PhD et al., "Deep Brain Stimulation in the Ventrolateral Thalamus/Subthalamic Area in Dystonia With Head Tremor," Movement Disorders, vol. 29, No. 7, 2014, pp. 953-959.
Racette, Brad A. et al., "Thalamic Stimulation for Primary Writing Tremor," J Neurol (2001) 248(5), pp. 380-382.
Reich, Martin M. et al., "Probabilistic Mapping of the Antidystonic Effect of Pallidal Neurostimulation: A Multicentre Imaging Study," Brain 2019; 142(5), pp. 1386-1398.
Sadnicka A. et al., "The Cerebellum in Dystonia—Help or Hindrance?" Clinical Neurophysiology 2012; 123(1), pp. 65-70.
Schjerling, Lisbeth et al., "A Randomized Double-Blind Crossover Trial Comparing Subthalamic and Pallidal Deep Brain Stimulation for Dystonia," Journal of Neurosurgery, Oct. 2013; 119(6), pp. 1537-1545.
Schrader, C., MD et al., "GPi-DBS May Induce a Hypokinetic Gait Disorder with Freezing of Gait in Patients with Dystonia," Neurology 2011; 77(5), pp. 483-488.
Sitsapesan, H. A. et al., "Deep Brain Stimulation for Tremor Resulting from Acquired Brain Injury," Journal of Neurology Neurosurgery and Psychiatry, vol. 85, No. 7, 2014, 13 pp.
Teo, James T. H. et al., "Neurophysiological Evidence for Cerebellar Dysfunction in Primary Focal Dystonia," Journal of Neurology Neurosurgery and Psychiatry, 2009; 80(1), pp. 80-83.
Tisch, S. et al., "Effect of Electrode Contact Location on Clinical Efficacy of Pallidal Deep Brain Stimulation in Primary Generalised Dystonia," J Neurol Neurosurg Psychiatry 2007; 78(12), pp. 1314-1319.
Tsui, Joseph K. et al,"Double-Blind Study of Botulinum Toxin in Spasmodic Torticollis," The Lancet, Aug. 2, 1986, pp. 245-247.
Volkmann, Jens et al., Pallidal Neurostimulation in Patients with Medication-Refractory Cervical Dystonia: A Randomised, Sham-Controlled Trial, Lancet Neurol 2014; 13(9), pp. 875-884.
Fayed, Islam et al., "Combination targeting of subthalamic nucleus and ventral intermediate thalamic nucleus with a single trajectory in deep brain stimulation for tremor-dominant Parkinson's disease," pp. 92-100.
Neudorfer, Clemens MD et al., "Combined Deep Brain Stimulation of Deep Brain Stimulation of Subthalamic Nucleus and Tremor-Dominant Parkinson's Disease Using a Parietal Approach," Neuromodulation 2019; 22: pp. 493-502.
Reinacher, Peter C. et al., "One Pass Thalamic and Subthalamic Stimulation for Patients with Tremor-Dominant Idiopathic Parkinson Syndrome (OPINION): Protocol for a Randomized, Active-Controlled, Double-Blinded Pilot Trial," JMIR Res Protoc 2018, vol. 7, Issue 1, E36, 11 pp.

* cited by examiner

FIG. 3A-C

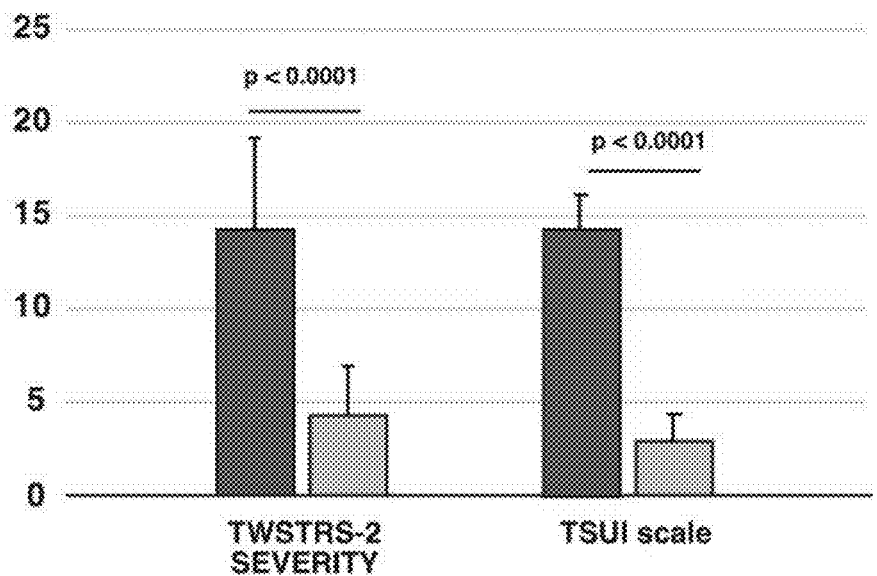
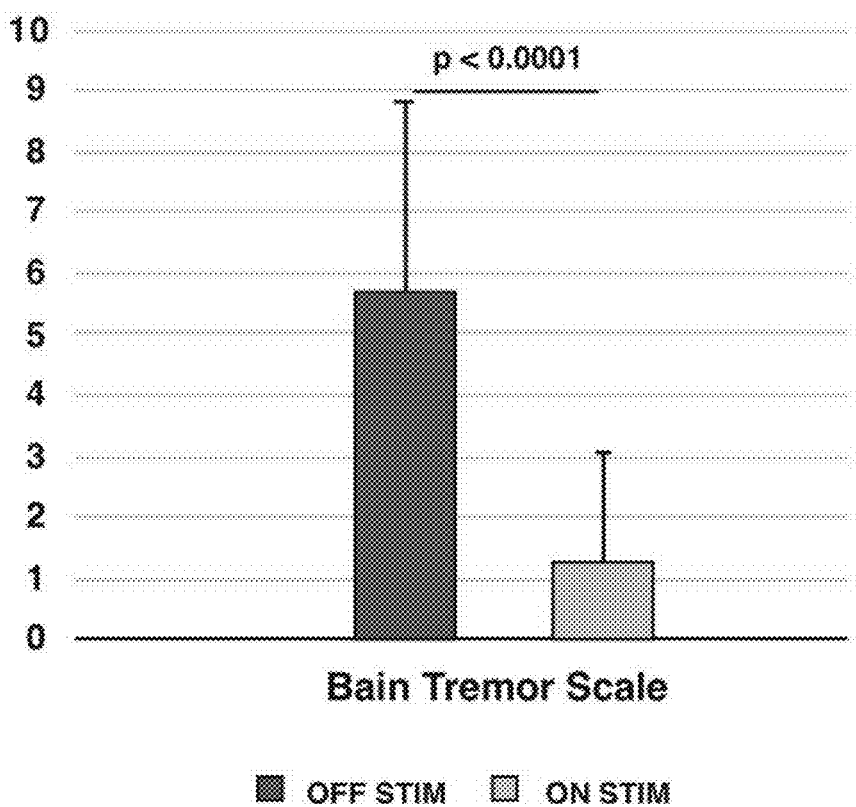
FIG. 6

DEEP BRAIN STIMULATION METHOD

CROSS-REFERENCE TO RELATED APPLICATION

This application claims priority of Great Britain Patent Application No. 2009230.0 filed Jun. 17, 2020, the entire contents of which are hereby incorporated by reference in this application.

The present invention relates to a method of deep brain stimulation for the treatment of cervical dystonia.

BACKGROUND

Cervical Dystonia (CD) is an incurable adult-onset neurological disorder that causes involuntary head twisting, turning and tremor due to abnormal activation of neck muscles.

CD is the most common form of adult-onset focal dystonia with a point prevalence of 28-183 cases/million, reaching up to 12.3/100,000 in the Irish population ≥20 years old. People with CD experience severe motor and psychological disability leading to impairment of activities of daily living, professional and social life.

Standard treatment is with life-long Botulinum Toxin requiring three monthly visits for injections, plus oral medications such as anticholinergic drugs or benzodiazepines, that might worsen cognitive function and attention.

In people with CD and severe disability, inadequately helped by botulinum toxin injections, Deep Brain Stimulation (DBS) of the internal segment of the Globus Pallidus (GPi) is a recognized treatment option. However, this treatment is completely ineffective in up to 35% of people, and even in those who respond there can be limited efficacy.

The motor thalamus was the main target for dystonia in the pre-DBS era and radiofrequency thalamic lesioning was effective in CD. Ventrolateral thalamus, specifically ventral intermediate nucleus (VIM) DBS also relieves dystonic head and hand tremor (Racette B A, Dowling J, Randle J, Mink J W. Thalamic stimulation for primary writing tremor. J Neurol 2001; 248(5): 380-2.; Kuncel A M, Turner D A, Ozelius L J, Greene P E, Grill W M, Stacy M A. Myoclonus and tremor response to thalamic deep brain stimulation parameters in a patient with inherited myoclonus-dystonia syndrome. Clin Neurol Neurosurg 2009; 111(3): 303-6.2009; Morishita T, Foote K D, Haq I U, Zeilman P, Jacobson C E, Okun M S. Should we consider Vim thalamic deep brain stimulation for select cases of severe refractory dystonic tremor. Stereotact Funct Neurosurg 2010; 88(2): 98-104.), but results for dystonia are inconsistent.

SUMMARY OF THE INVENTION

Problem to Be Solved

The present invention aims to provide means to treat cervical dystonia. In particular, to provide a method to more reliably alleviate motor and non-motor symptoms of cervical dystonia. Furthermore, the invention aims to reduce symptoms of tonic cervical dystonia, as well as tremor dystonia.

Means to Solve the Problem

In accordance with the present invention, a deep brain stimulation method for use in the treatment of cervical dystonia, comprises inserting a stimulation device into the brain of a patient, the stimulation device being configured to provide electrical stimulation to affect first and second stimulation targets within the brain; the first stimulation target being the subthalamic nucleus (STN); and the second stimulation target being either the ventral intermediate nucleus (VIM), or the ventralis oralis posterior thalamus (VOP), or both the ventral intermediate nucleus (VIM) and the ventralis oralis posterior thalamus (VOP). This stimulation of two target nuclei can quickly relieve symptoms of cervical dystonia.

Optionally, the stimulation device is inserted on a posterior frontal extraventricular trajectory going through premotor cortex. This trajectory enables effective targeting of the two stimulation target nuclei.

Optionally, the method comprises controlling the stimulation device to activate the first stimulation target and the second stimulation target simultaneously.

Optionally, the method comprises transmitting electrical pulses generated by a pulse generator through an electrode lead to one or more electrical contacts of the stimulation device.

Optionally, the method comprises providing an electrical stimulation using a single electrical contact of the electrode lead to affect both the first stimulation target and the second stimulation target.

Optionally, the method comprises providing electrical stimulations using a first electrical contact of the electrode lead to affect the first stimulation target and a second electrical contact of the electrode lead to affect the second stimulation target. This enables efficient stimulation of multiple targets in the brain without the need to use a different electrode lead for each stimulation target. Furthermore, this means that a single insertion point is needed to insert the electrode lead to stimulate two stimulation targets, and the patient does not require multiple insertion locations per hemisphere of the brain.

Optionally, the first electrical contact contacts the first stimulation target and the second electrical contact contacts the second stimulation target during the electrical stimulations.

Optionally, the method comprises applying electrical stimulation defined by first stimulation parameters to the first electrical contact and applying electrical stimulation defined by second stimulation parameters to the second electrical contact, wherein the first and second stimulation parameters are identical to each other for each of one or more of the following: frequency, pulse width and current.

Optionally, the electrode lead comprises eight electrical contacts disposed at separate locations on the electrode lead.

Optionally, the one or more electrical contacts are disposed to span between 9 mm and 20 mm in a longitudinal direction of the electrode lead.

Optionally, the one or more electrical contacts comprises a plurality of electrical contacts each having a length of between 0.9 mm and 2 mm and being spaced between 0.25 mm and 2 mm apart along the electrode lead. With multiple electrical contacts having this size and spacing, the electrical field can be appropriately shaped to activate the stimulation.

Optionally, each of the one or more electrical contacts continuously surrounds an axis of the electrode lead. With this configuration the target area can be stimulated effectively when the electrical contact is disposed in the stimulation target area, because the stimulation is not directional.

Optionally, the method comprises applying electrical stimulation at a frequency greater than or equal to 60 Hz and less than or equal to 255 Hz frequency and a pulse width greater than or equal to 20 µs and less than or equal to 450 µs. Preferably, the frequency is greater than or equal to 120

Hz and less than or equal to 180 Hz frequency and the pulse width is greater than or equal to 30 μs and less than or equal to 90 μs.

Optionally, the stimulation device is configured to affect a third stimulation target in the brain, the third stimulation target being the Zona Incerta (ZI). This target has been shown to relieve symptoms of cervical dystonia, when stimulated in combination with the stimulation of the other stimulation targets.

The method may be applied for the treatment of cervical dystonia. The method may be applied for the treatment of tonic cervical dystonia. The method may be used for the treatment of non-motor symptoms of cervical dystonia.

Optionally, the method comprises inserting the stimulation device into a first hemisphere of the brain and a second hemisphere of the brain, wherein the stimulation device is configured to provide electrical stimulation to affect both hemispheres of the brain of the patient.

The patent or application file contains at least one drawing executed in color. Copies of this patent or patent application publication with color drawing(s) will be provided by the Office upon request and payment of the necessary fee.

The present invention will now be described with reference to exemplary embodiments and the accompanying figures, in which.

Figure 5:
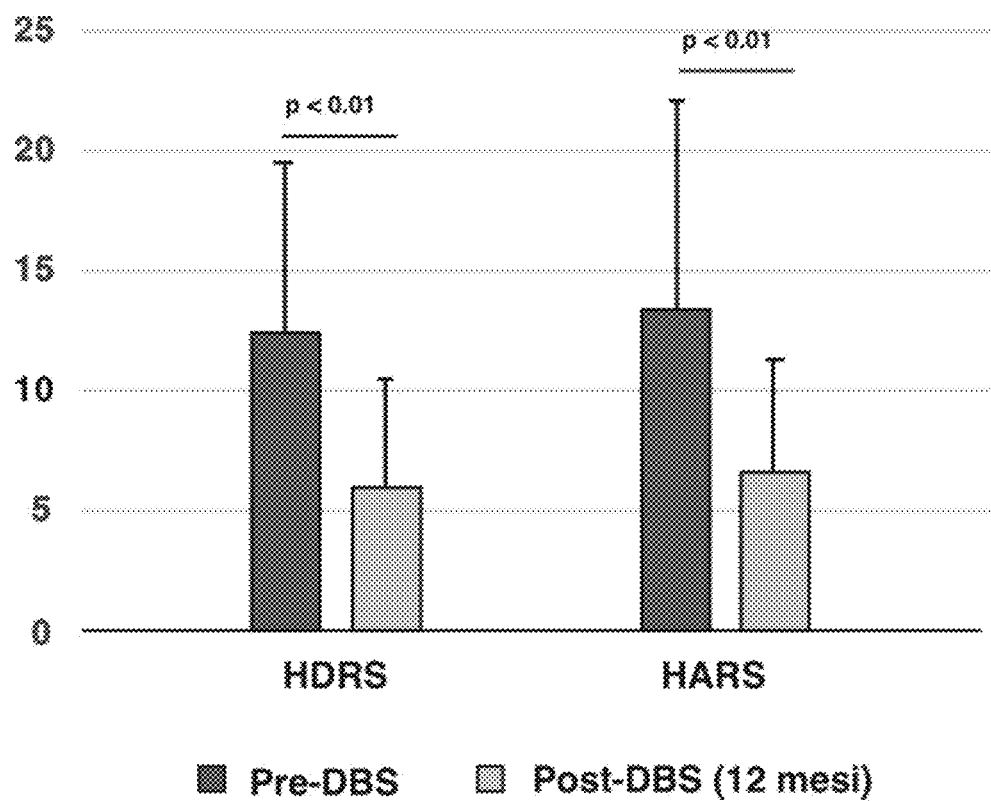
Figure 7:
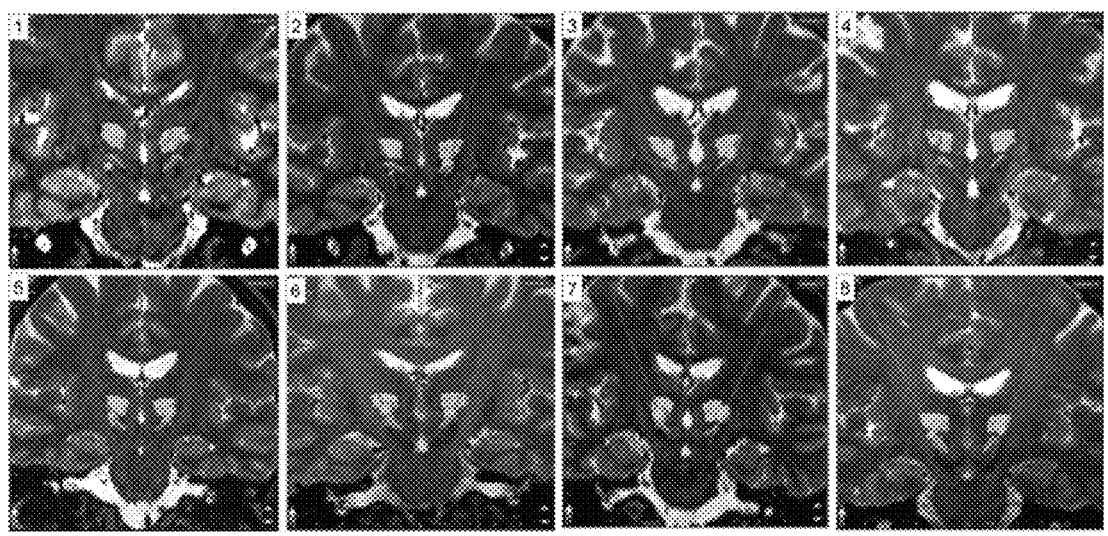

FIG. 3A-C are schematic diagrams of electrode leads according to embodiments of the present invention;

FIG. 4A-D are bar graphs showing levels of motor (severity of cervical dystonia by Toronto Western Spasmodic Torticollis Rating Scale, TWSTRS, and Tsui scale) non-motor symptoms (scales for pain, sleep and psychiatric symptoms) of cervical dystonia before stimulation (pre-DBS) and after stimulation (post-DBS) from data gathered in the example study;

FIG. 5 are bar graphs of Hamilton Depression and Hamilton Anxiety rating scales before stimulation (pre-DBS) and after stimulation (post-DBS) from data gathered in the example study;

FIG. 6A-B are bar graphs of motor variables at STIM-ON compared to STIM-OFF from data gathered in the example study;

FIG. 7 is electrode positions and aggregated volumes of tissue activation (orange) by patient in relation to STN (green), VIM (pink) and red nuclei in the coronal plane, anterior foremost of the patient's T-2 weighted MRI from data gathered in the example study;

FIG. 8A-B are graphs of the angular velocity and tremor severity at STIM-ON and STIM-OFF from electromyogram data gathered in the example study;

DETAILED DESCRIPTION

Overview

Cervical Dystonia (CD) is an incurable adult-onset neurological disorder that causes involuntary head twisting, turning and tremor due to abnormal activation of neck muscles. There are three main phenotypic patterns of CD. Most commonly, patients develop complex biaxial or triaxial head deviation, with a mixture of these components that alternate as phasic movements: phasic-CD. Alternatively, some patients develop sustained, relatively fixed tonic and often painful abnormal head postures: tonic-CD. Lastly, some patients have a phenotype dominated by tremor where head turning is present as well but is a secondary feature: tremulous-CD.

One form of treatment for cervical dystonia is deep brain stimulation (DBS). DBS involves inserting a stimulation device into the brain of a patient to affect at least one target region within the brain when stimulation is applied.

The stimulation device may comprise an electrode lead. Electrical pulses may be transmitted through the electrode lead to one or more electrical contacts of the stimulation device. The electrode lead is inserted such that the electrode contacts are in proximity to, or in contact with, the stimulation target areas of the brain. Thus, electrical pulses transmitted to the electrode contacts affect the stimulation target regions of the brain.

Figure 1:
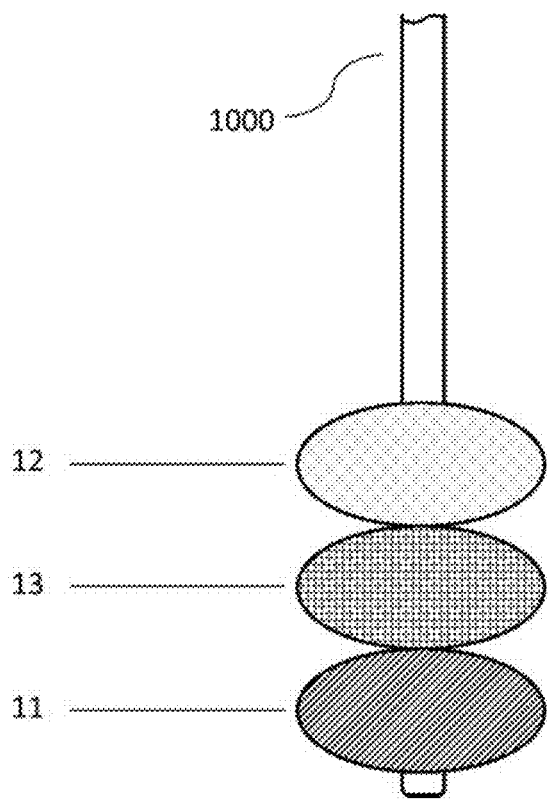
FIG. 1 is a stimulation device intersecting first, second and third stimulation targets according to an embodiment of the present invention.

A method of treatment for cervical dystonia involves inserting the stimulation device 1000, as shown in FIG. 1, such that it is disposed to provide electrical stimulation to affect two separate nuclei within the brain.

Electrode Lead Trajectory/Placement

In the present method, the stimulation device 1000 is inserted into place within the brain such that the inserted device is configured to provide electrical stimulation to affect two stimulation targets 11, 12 within the brain. The stimulation targets 11, 12 comprise at least two separate nuclei within the brain.

In particular, the first stimulation target 11 is the subthalamic nucleus (STN). The second stimulation target 12 may be either the ventral intermediate nucleus (VIM), or the ventralis oralis posterior thalamus (VOP), or both the ventral intermediate nucleus (VIM) and the ventralis oralis posterior thalamus (VOP). In other words, it is preferable to stimulate the STN and either the VIM, or the VOP, or the VIM/VOP interface.

The stimulation device may be configured to affect a third stimulation target 13 in the brain, the third stimulation target being the Zona Incerta (ZI).

In order to affect the above-mentioned stimulation targets, it is preferable to insert the stimulation device on a posterior frontal extraventricular trajectory going through premotor cortex.

To insert the stimulation device in the brain, surgery is performed on the patient. During surgery a base ring and stereotactic localiser may be applied to the patient's head while the patient is under general anaesthesia. A stereotactic computed tomography (CT) scan may then be performed and the CT scan images may be combined with magnetic resonance imaging (MRI) images. Image fusion, trajectory planning and stereotactic transformation may be undertaken. The CT and MRI images can be used to identify the position of the anterior and posterior commissures (AC, PC) and midline. The ventral intermediate (VIM) motor thalamus is targeted, for example by using classic AC-PC stereotactic co-ordinates (x=+/−11, y=−4, z=0). A biopsy needle may be inserted down the stereotactic frame to form a track to target in the brain before electrode lead insertion. The STN may be directly targeted at the superior, posterior third at the axial level of the red nuclei.

The above-described method to insert the stimulation device is preferable, however, alternative methods may be used to perform the DBS surgery and associated scans. For example, a frameless technique may be applied, with fiducials screwed into the skull. Furthermore, MRI images may be sufficient to plan the trajectory, without the need to also perform CT scans and use CT scan images.

The stimulation device is preferably inserted to intersect the STN target as close through the VIM target as possible through an ipsilateral, transfrontal trajectory anterior to the anatomically delineated primary motor cortex. If a preliminary trajectory bisected a sulcus then it may be modified to favour safety with the entry point relocated to a gyms. Similarly, transventricular ependymal breach and associated haemorrhage risk may be avoided by adjusting entry points more laterally. Such adjustments could shift upper electrode contacts from VIM to ventralis oralis posterior thalamus (VOP) or the VIM/VOP interface.

Electrode Leads

Figure 2:
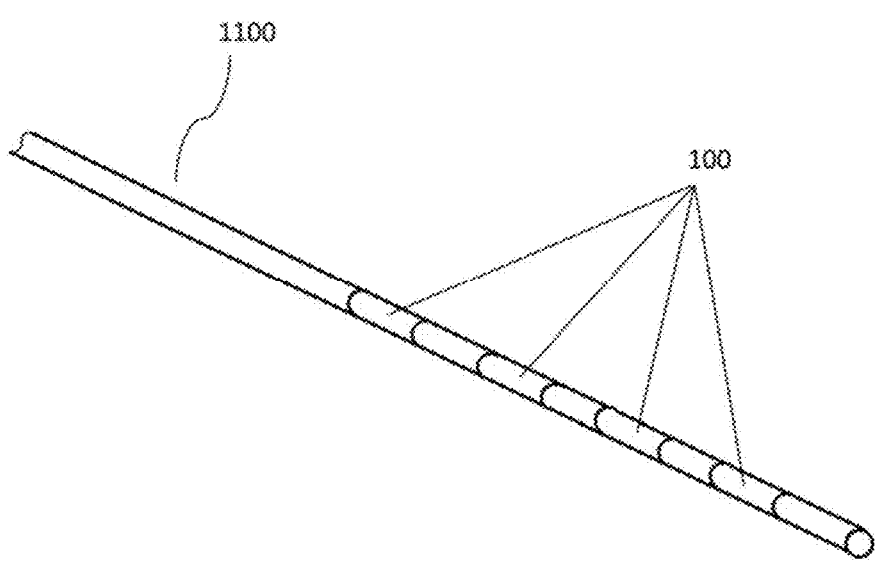
FIG. 2 is a view of the electrode lead of the stimulation device of FIG. 1.
Figure 3:
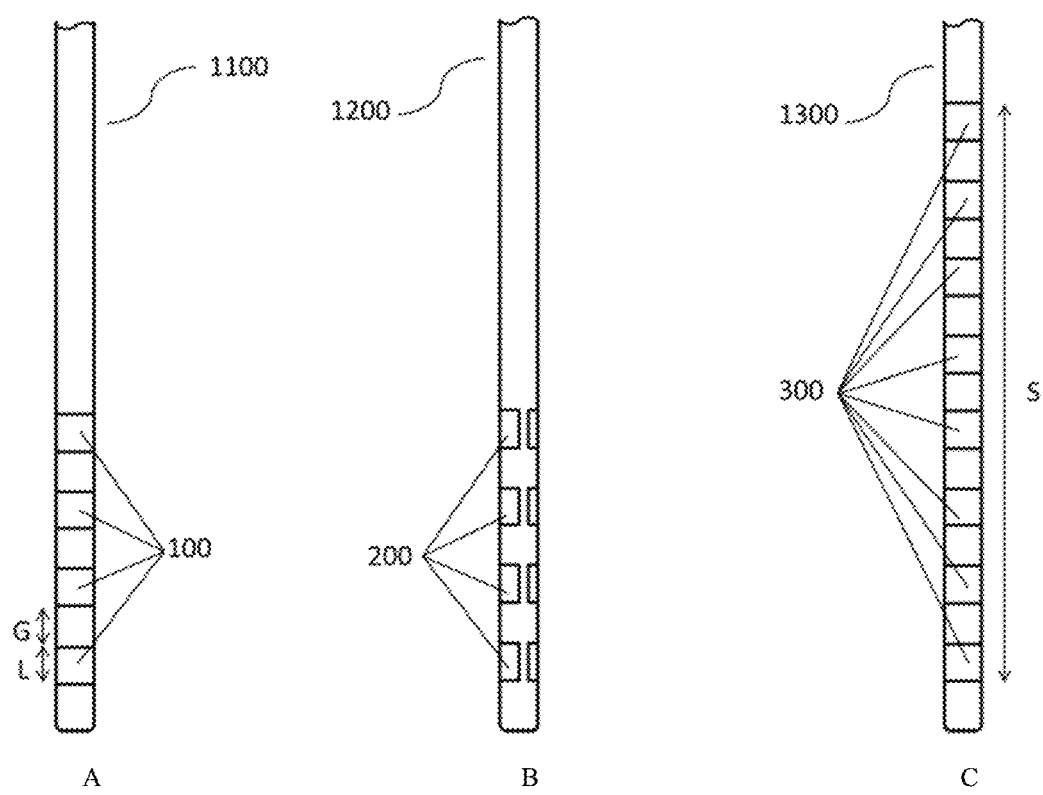

The stimulation device may comprise an electrode lead 1100, 1200, 1300 comprising one or more electrode contacts 100, 200, 300, as shown in FIGS. 2 and 3. The electrode lead 1100, 1200, 1300 is configured to transmit electrical pulses to the electrode contacts 100, 200, 300.

The electrode lead may comprise a single electrical contact configured to affect both the first stimulation target and the second stimulation target when the stimulation device is inserted in the brain of the patient. The electrode lead may therefore be provided with an electrode contact with a length greater than or equal to the distance between the two stimulation targets.

Alternatively, the electrode lead may comprise a first electrical contact of the electrode lead to affect the first stimulation target and a second electrical contact of the electrode lead to affect the second stimulation target. The electrode lead may therefore be provided with at least two electrode contacts, such that the first electrical contact contacts the first stimulation target and the second electrical contact contacts the second stimulation target when the stimulation device is inserted in the brain.

The electrode lead may be configured for selective activation of each of the electrode contacts. As such, electrical stimulation defined by first stimulation parameters may be applied to the first electrical contact and electrical stimulation defined by second stimulation parameters may be applied to the second electrical contact. The first and second stimulation parameters may optionally be identical to each other for each of one or more of the following: frequency, pulse width and current.

The electrode lead 1100, 1200, 1300 may comprise a plurality of electrical contacts each disposed at separate locations along the axial direction of the electrode lead, as shown in FIGS. 2 and 3.

The one or more electrical contacts may comprises a plurality of electrical contacts 100 each having a length (L) of between 0.9 mm and 2 mm and being spaced with a gap (G) of between 0.25 mm and 2 mm apart along the electrode lead, as shown in FIG. 3A. Preferably, the electrical contacts are each 1.5 mm in length (L) spaced with a gap (G) of 0.5 mm apart along an axis of the electrode lead.

The one or more electrical contacts 300 are preferably disposed to have a total span (S) between 9 mm and 20 mm in a longitudinal direction of the electrode lead, as shown in FIG. 3C.

Each of the one or more electrical contacts 100, 300 may continuously surround an axis of the electrode lead, as shown in FIGS. 2, 3A and 3C.

Alternatively, the one or more electrical contacts 200 may be disposed at discrete radial locations around the axis of the electrode lead 1200. For example, there may be more than one electrode contact 200 disposed around the axis of the electrode lead, as shown in FIG. 3B.

The electrode lead is preferable configured such that the user may control which electrode contacts are activated. With a larger number of electrode contacts disposed along and/or around the electrode lead, the user has more control over the location at which stimulation is applied. Thus, it is possible for the user to tune the affected stimulation region after surgery by selective stimulation of electrode. With multiple electrodes disposed at different axial positions around the electrode lead, it is possible for the user to determine which direction the stimulation is provided around the electrode lead. Thus there is improved directionality and fidelity of the stimulation.

Stimulation Parameters

The method may comprise the use of a pulse generator to generate electrical pulses. The electrode pulses may be transmitted through the electrode lead to the one or more electrical contacts of the stimulation device.

The method may comprise applying electrical stimulation at a certain frequency, pulse width and current amplitude. These stimulation parameters may be selected by the user/doctor. The pulse generator is therefore configured to generate electrical pulses according to the selected stimulation parameters. The pulse generator may be implanted in the chest wall of the patient.

The frequency of the electrical pulses is preferably between 60 and 255 Hz.

The frequency may be similar to the typical frequency range used in GPi stimulation. For example, the frequency of the electrical pulses may be between 75 and 85 Hz.

Preferably, the frequency of the electrical pulses is greater than or equal to 120 Hz and less than or equal to 180 Hz. More preferably, the frequency of the electrical pulses is between 120 Hz and 170 Hz. Yet more preferably, the frequency of the electrical pulses is between 120 Hz and 160 Hz. Yet more preferably, the frequency of the electrical pulses is between 120 Hz and 150 Hz.

The pulse width may be greater than or equal to 20 μs and less than or equal to 450 μs. The pulse width is preferably greater than or equal to 30 μs and less than or equal to 90 μs. More preferably, the pulse width is between 40 μs and 80 μs. Yet more preferably, the pulse width is between 50 μs and 70 μs. Yet more preferably, the pulse width is between 55 μs and 65 μs.

The current is preferably greater is preferably greater than or equal to 0.5 mA and less than or equal to 5 mA. More preferably, the current is between 1 mA and 4 mA.

The stimulation device may be configured to activate only the selected electrical contacts. Thus, the stimulation device may be inserted such that the electrode contacts are in proximity to a plurality of potential stimulation target areas of the brain. The user/doctor may therefore identify the most appropriate electrode contact to activate in order to affect the selected stimulation target area of the brain.

The method preferably comprises controlling the stimulation device to activate the first stimulation target and the second stimulation target simultaneously. With this approach, the first and second stimulation targets are affected by stimulation at approximately the same time. However, the stimulation device may be configured to deliver interleaving stimulation, wherein the stimuli are applied to the two stimulation targets at different times.

The method may be applied by inserting the stimulation device into a first hemisphere of the brain, wherein the stimulation device is configured to provide electrical stimulation to affect the first hemisphere of the brain of the patient. Preferably, the method also comprises inserting the stimulation device into a second hemisphere of the brain, wherein the stimulation device is configured to provide electrical stimulation to affect both the first and second hemispheres of the brain of the patient.

The method, stimulating both the first and second stimulation targets, has shown a rapid time course of improvement. The speed of patient improvement enables the neurologist to observe the influence stimulation is having on the patient's symptoms and to control the stimulation parameters to invoke further improvement. The fast, and in some cases immediate, symptomatic improvement thus enables the neurologist to directly target motor and non-motor aspects, rather than be guided only by the threshold for side-effects. As such, the stimulation parameters may be more effectively tailored to the patient based on their response to initial stimulation and further alleviation of symptoms may be achieved.

Cervical Dystonia

The method may be applied for the treatment of symptoms of cervical dystonia. The method may be applied for the treatment of tonic symptoms of cervical dystonia. The method may be used to treat non-motor symptoms of cervical dystonia, including pain, anxiety, depression and sleep disturbances.

EXAMPLE STUDY

Method

Patients with CD, attending the Advanced Movement Disorders Therapy Clinic at St George's University Hospital, were eligible for the study if they met the following inclusion criteria: clinical evidence of Tonic-Painful variant of CD or Tremulous variant of CD; age 14-75 years; disease duration≥3 years; presence of severe disability and poor quality of life (QoL), despite optimal botulinum toxin therapy and/or oral medications.

Exclusion criteria were: clinical evidence of phasic variant of CD; previous brain surgery; cognitive impairment as per neuropsychological testing results; diagnosis of major depression; marked brain atrophy (detected by brain MRI); presence of medical conditions that could increase surgical risk.

Institutional ethics approval was obtained (IRAS 259146). The study was conducted in accordance with the Declaration of Helsinki. Each participant provided written informed consent before study participation.

Demographical and Clinical Variables

For each subject, the following demographic and clinical data were collected at the time of study entry: age, gender, education level, weight, age at disease onset, disease duration, current medications, dosage of Botulinum toxin (BoNT) at last follow-up.

Detailed evaluation of quality of life, motor and non-motor symptoms severity, and motor and non-motor fluctuations was carried out with specific patient's or clinician's administered rating instruments. Specifically:

Comprehensive Cervical Dystonia Rating scale (Comella C L, Fox S H, Bhatia K P, Perlmutter J S, Jinnah H A, Zurowski M, et al. Development of the Comprehensive Cervical Dystonia Rating Scale: Methodology. Mov Disord Clin Pract 2015; 2(2): 135-41.). This scale includes 4 subscales which account for CD severity (TWSTRS-2 severity score), disability, pain (TWSTRS-Pain) and psychiatric symptoms (TWSTRS-Psy).

Tsui scale (Tsui J K, Eisen A, Stoessl A J, Calne S, Calne D B. Double-blind study of botulinum toxin in spasmodic torticollis. Lancet 1986; 2(8501): 245-7.), including the sub-items for tremor, and Bain Tremor Score (BTS) (Bain P G, Findley L J, Atchison P, Behari M, Vidailhet M, Gresty M, et al. Assessing tremor severity. J Neurol Neurosurg Psychiatry 1993; 56(8): 868-73.).

Burke-Fahn-Marsden Rating Scale (BFMDRS) (Burke et al., 1985).

Craniocervical Dystonia Questionnaire-24 (CD-24), for quality of life (QoL) (Muller J, Wissel J, Kemmler G, Voller B, Bodner T, Schneider A, et al. Craniocervical dystonia questionnaire (CDQ-24): development and validation of a disease-specific quality of life instrument. J Neurol Neurosurg Psychiatry 2004; 75(5): 749-53.).

Pittsburgh Quality of Sleep Index (PSQI), for sleep disturbances.

Hamilton Depression and Hamilton Anxiety rating scales (HDRS and HARS), for depression and anxiety.

Study Design

Subjects were evaluated pre-operatively (T0) and at 3 (T3), 6 (T6) and 12-months follow-up (T12). At these time-points evaluation of dystonia severity (by TWSTRS-2, Tsui scale and BTS) and side effects of DBS was carried out. Assessment of motor and non-motor symptoms, disability and quality of life was carried-out at T0 and T12. At T12, assessments were performed both with neurostimulator switched ON (STIM ON) and OFF (STIM OFF) and they included also included performance of wireless EMG and kinematic of head movements.

Clinical assessments were videotaped at each time point and all videos were blindly assessed at the end of the study by two independent dystonia experts who were unaware of order of the examinations. Each rater performed video assessment of TWSTRS-2, Tsui scale and BTS.

Wireless EMG and kinematic analysis at T12 comparing STIM OFF and STIM ON condition. Analysis was performed by another independent investigator (A. S.) blinded to stimulation conditions.

Surgical Procedure

The 8 patients underwent surgery from July 2018 to December 2019. 1.5 Tesla axial MRI was acquired under general anaesthesia 7-11 months before surgery on a clinical scanner (Philips® Achieva, Philips Ltd, Netherlands) with routine 1 mm voxel DBS planning sequences (T1, T2, FLAIR, SWI, FGATIR). For surgery, a Cosman-Roberts-Wells (CRW®; Integra®, USA) base ring and stereotactic localiser were applied to the patient's head under general anaesthesia. A stereotactic CT scan (GE Revolution® 64, GE Healthcare, USA) with 0.625 mm slice reconstruction was then performed and the MRI scans were volumetrically fused to it and each other. Image fusion, trajectory planning and stereotactic transformation were undertaken using Renishaw Neuroinspire™ planning software (v5, Renishaw PLC, UK). Anterior and posterior commissures (AC, PC) and midline were defined and ventral intermediate (VIM) motor thalamus targeted using classic AC-PC stereotactic co-ordinates ($x=+/-11$, $y=-4$, $z=0$). The STN were directly targeted to their superior, posterior third at the axial level of the red nuclei. Trajectories were carefully planned to go to the STN target as close through the VIM target as possible through an ipsilateral, transfrontal trajectory anterior to the anatomically delineated primary motor cortex. If a preliminary trajectory bisected a sulcus then it was modified to favour safety with the entry point relocated to a gyms. Similarly, transventricular ependymal breach and associated haemorrhage risk were avoided by adjusting entry points more laterally. Such adjustments could shift upper electrode contacts from VIM to ventralis oralis posterior thalamus (VOP) or the VIM/VOP interface (see Table 1). The final treatment stereotactic coordinates for the bilateral targets were transferred to a pair of CRW® stereotactic phantoms (Integra®, USA).

Surgery was performed under general anaesthesia. The head was slightly inclined to facilitate access, but the patient kept as supine as possible to emulate MM position and minimise cerebrospinal fluid egress and brain shift. After minimal hair shave and 3 cm linear scalp incision, a 2.7 mm twistdrill craniostomy was performed before insertion of a closed Nashold rigid biopsy needle (Integra®) down the CRW stereotactic frame to form a track to target in the brain before electrode lead insertion. Boston Scientific DB-2201, 30cm long, non-segmented, octopolar electrode leads with 0.5 mm spaced contacts of 1.5 mm length (Boston Scientific, USA) were bilaterally implanted (left side first) with the tips 2 mm below the STN targets. One electrode lead was advanced through both predetermined VIM and STN targets per hemisphere. Each electrode lead was fixed by a 13 mm Synthes miniplate (Johnson & Johnson®, USA) and the craniostomy sealed by bone wax. After repeat CT confirming accurate electrode position, the stereotactic base ring was removed and 50 cm extension leads were tunnelled through a left parietal incision to a rechargeable (Gevia®, Boston Scientific) pulse generator implanted in the left chest wall. An image verified approach was taken with neither intra-operative stimulation nor electrophysiological recording during the asleep surgery. General anaesthetic time was approximately three hours for the whole surgery, both the stages of electrode lead insertion and of pulse generator implantation including transfers between operating theatre and CT scan. Inpatient hospital stay was three to four days.

Lead Localization Determination

Effective stereotactic coordinates were obtained at last clinical reprogramming by retrospective calculation of active contact points from the immediate post-operative CT using Renishaw Neuroinspire™ v6 software. These are displayed in Table 1. Supplementary FIG. 1 shows active uppermost and lowermost bipolar montage electrode contacts by patient, with actual electrode contact positions on CT superimposed upon T2-weighted axial, coronal and sagittal MRI. Three-dimensional models of VIM, ZI, red nuclei and STN were generated from fusion of all the MRI and CT images using individualised segmentation software autosegmentation algorithms without manual adjustment (Brainlab Elements™ Stereoplan v2 and Guide-XT software, Brainlab®, Germany). 3D models containing both the known lead geometry and the position of each contact were generated. For comparison between individuals, active contacts of each patient were aggregated in Brainlab® Atlas space to indicate areas of high active contact overlap probability.

TABLE 1

| Subject | Contact | contact number | x | y | z | Location |
| --- | --- | --- | --- | --- | --- | --- |
| 1 | Left lower | 3 | −11.0 | −5.2 | −1.6 | STN |
|  | Left upper | 7 | −13.9 | −4.3 | 5.7 | VIM |
|  | Right lower | 2 | 11.2 | −3.7 | −3.1 | STN |
|  | Right upper |  |  |  |  |  |
| 2 | Left lower | 2 | −10.6 | −3.1 | −3.5 | STN |
|  | Left upper | 3 | −11.4 | −2.9 | −1.6 | ZI |
|  | Right lower | 2 | 11.5 | −4.6 | −5.7 | STN |
|  | Right upper | 4 | 12.9 | −4.0 | −1.9 | ZI |
| 3 | Left lower | 4 | −13.2 | −3.4 | −0.7 | ZI |
|  | Left upper | 6 | −14.6 | −2.4 | 2.7 | VOP |
|  | Right lower | 3 | 10.6 | −4.1 | 0.7 | ZI |
|  | Right upper | 5 | 12.2 | −3.2 | 4.1 | VIM |

TABLE 1-continued

| Subject | Contact | contact number | x | y | z | Location |
| --- | --- | --- | --- | --- | --- | --- |
| 4 | Left lower | 6 | −16.7 | −0.3 | 4.7 | VOP |
|  | Left upper | 7 | −17.3 | 0.1 | 6.4 | VOP |
|  | Right lower |  |  |  |  |  |
|  | Right upper | 7 | 14.5 | 1.3 | 4.5 | VOP |
| 5 | Left lower | 3 | −12.1 | −4.3 | 0.7 | STN |
|  | Left upper | 6 | −14.2 | −3.1 | 6.2 | VOP |
|  | Right lower | 3 | 12.5 | −3.4 | 0.3 | STN |
|  | Right upper | 5 | 13.8 | −2.9 | 4.0 | VOP |
| 6 | Left lower | 3 | −13.8 | −2.6 | 0.2 | ZI |
|  | Left upper |  |  |  |  |  |
|  | Right lower | 4 | 13.5 | −2.5 | 0.2 | VOP |
|  | Right upper |  |  |  |  |  |
| 7 | Left lower | 6 | −13.9 | −3.0 | 1.7 | VOP |
|  | Left upper | 7 | −14.8 | −2.3 | 3.7 | VOP |
|  | Right lower | 5 | 10.8 | −3.1 | 1.4 | ZI |
|  | Right upper | 6 | 11.4 | −2.7 | 3.4 | VOP |
| 8 | Left lower | 6 | −14.0 | −2.4 | 3.6 | VOP |
|  | Left upper | 7 | −14.5 | −2.0 | 5.5 | VOP |
|  | Right lower | 5 | 14.6 | −2.2 | 3.4 | ZI |
|  | Right upper |  |  |  |  |  |

DBS Programming

The first post-operative assessment was scheduled at 3 weeks after surgery. An unblinded neurologist performed monopolar review of each stimulation contact (at 130 Hz, 60 µs pulse width) in order to set the threshold for side effects. Neurological assessment at first programming session was performed by the unblinded programming neurologist. As STN/VIM DBS provided immediate change in clinical symptoms, the contact providing the best clinical effect on head posturing and tremor with the highest threshold for side effects could be chosen. Settings were adjusted over subsequent programming sessions in order to provide maximal control of motor and non-motor (pain) symptoms. Number of programming sessions, number and site of activated contacts, amplitude of current (mA), pulse width (µs) and frequency (Hz) were collated for each patient.

Statistical Analysis

After checking for normal distribution of the variables by Kolmogorov-Smirnov test, paired comparisons were performed by either t-test or Wilcoxon for continuous variables and Chi-square or Fisher exact test for categorical data. The primary endpoint was the change of TWSTRS-2 severity score on blinded videotaped assessment at T12 compared to baseline (T0). All other variables were secondary endpoints.

Significance level was set at $p<0.05$. Statistical analysis was performed with Statview, version 5.0. Data are shown in mean and standard deviation (SD).

Results

Clinical Data

Eight CD patients were enrolled and 5 completed the 12-months follow-up (results shown in figures). The eight patients were women, age range 41-70 years, disease duration range 4-25 years.

At the first programming session, unblinded evaluation disclosed significant improvement of TWSTRS-2 severity score ($p<0.005$), TSUI subscore for tremor ($p<0.001$) and TWSTRS-2 pain score ($p<0.005$).

Stimulation parameters and sites of stimulation at last follow-up are shown in Table 1 and Table 2. Range of pulse width varied from 30 mcs to 90 mcs. Current amplitude was often asymmetrical. All patients had activation of at least two brain targets, among STN, ventrolateral thalamus (VIM or VoP) and Zona Incerta (ZI). Combined stimulation of at least two targets were set on at least one side in all patients.

All tonic-CD patients (except one) had another active contact in the STN which was effective in treating pain and improving head range of motion. Combined stimulation led to a large benefit in the range of motion that was impaired at baseline in all patients, mostly in tonic-CD. Supplementary videos online show one patient with Tonic-CD and one patient with Tremor-CD before and after STN/VIM DBS (STIM OFF and STIM-ON).

Figure 4:
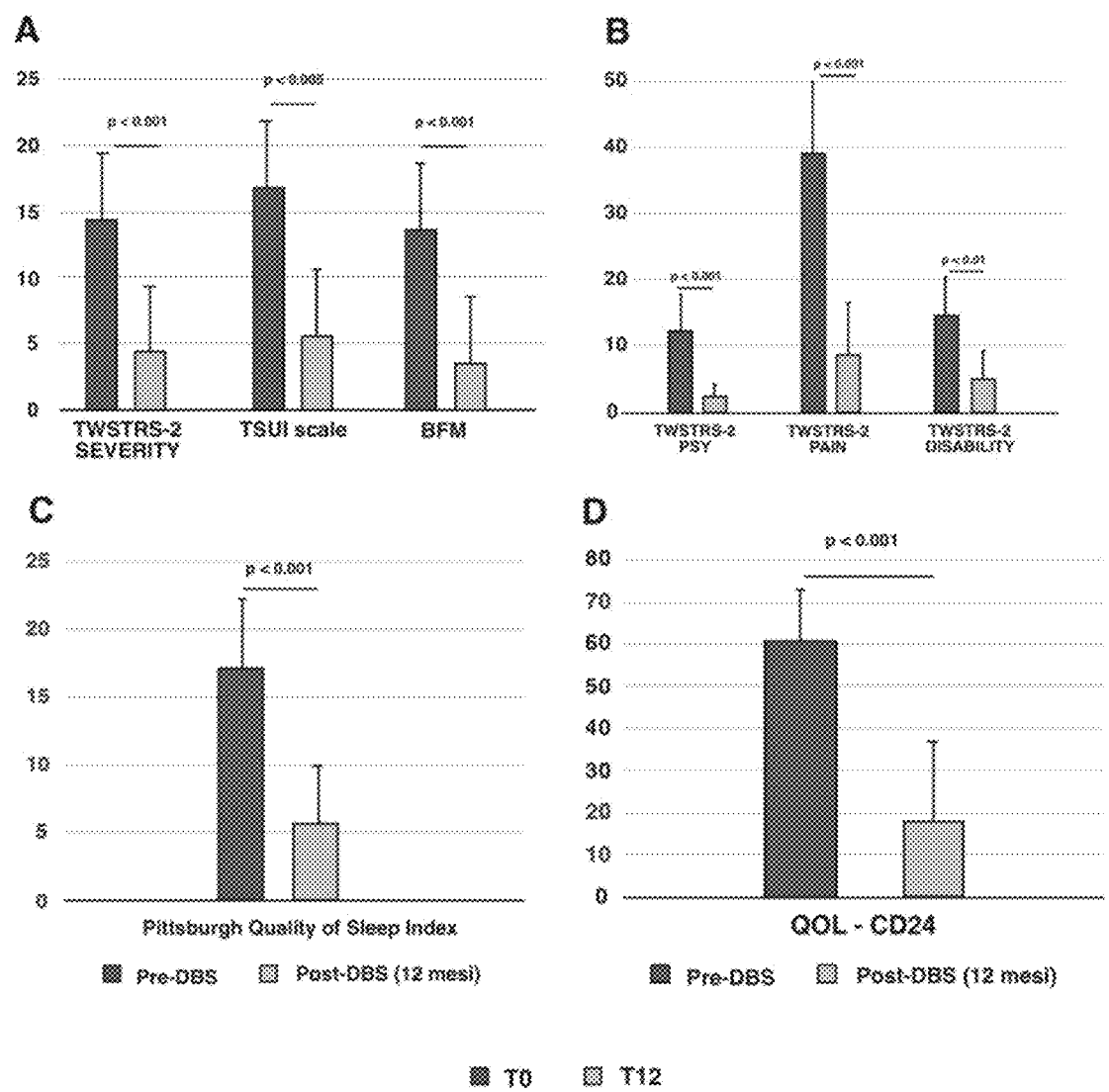

Blinded assessment of TWSTRS-2 severity score at T12 compared to T0 showed a significative reduction in motor disability ($p<0.001$) (FIG. 4A). Comparable results were obtained for BFMDRS and TSUI scale ($p<0.005$) at T12 compared to T0. At T12 psychiatric symptoms (TWSTRS-2 PSY), pain (TWSTRS-2 PAIN) activities of daily living (TWSTRS-2 DISABILITY) (FIG. 4B) improved as well. Sleep as per PSQI and QoL as per CD-24 significantly improved at T12 (FIG. 4C-D). Burden of depression and anxiety assessed by HDRS and HARS was significantly lower at T12 (FIG. 5).

Blinded analysis of motor variables at STIM-ON was compared to STIM-OFF. TWSTRS-2 severity score ($p<0.0001$), tremor subitem of TSUI scale ($p<0.001$) and of Bain Tremor score ($p<0.01$) were all significantly lower in STIM-ON compared to STIM-OFF (FIG. 6).

Electromyogram (EMG)/Kinematic Data

Figure 8:
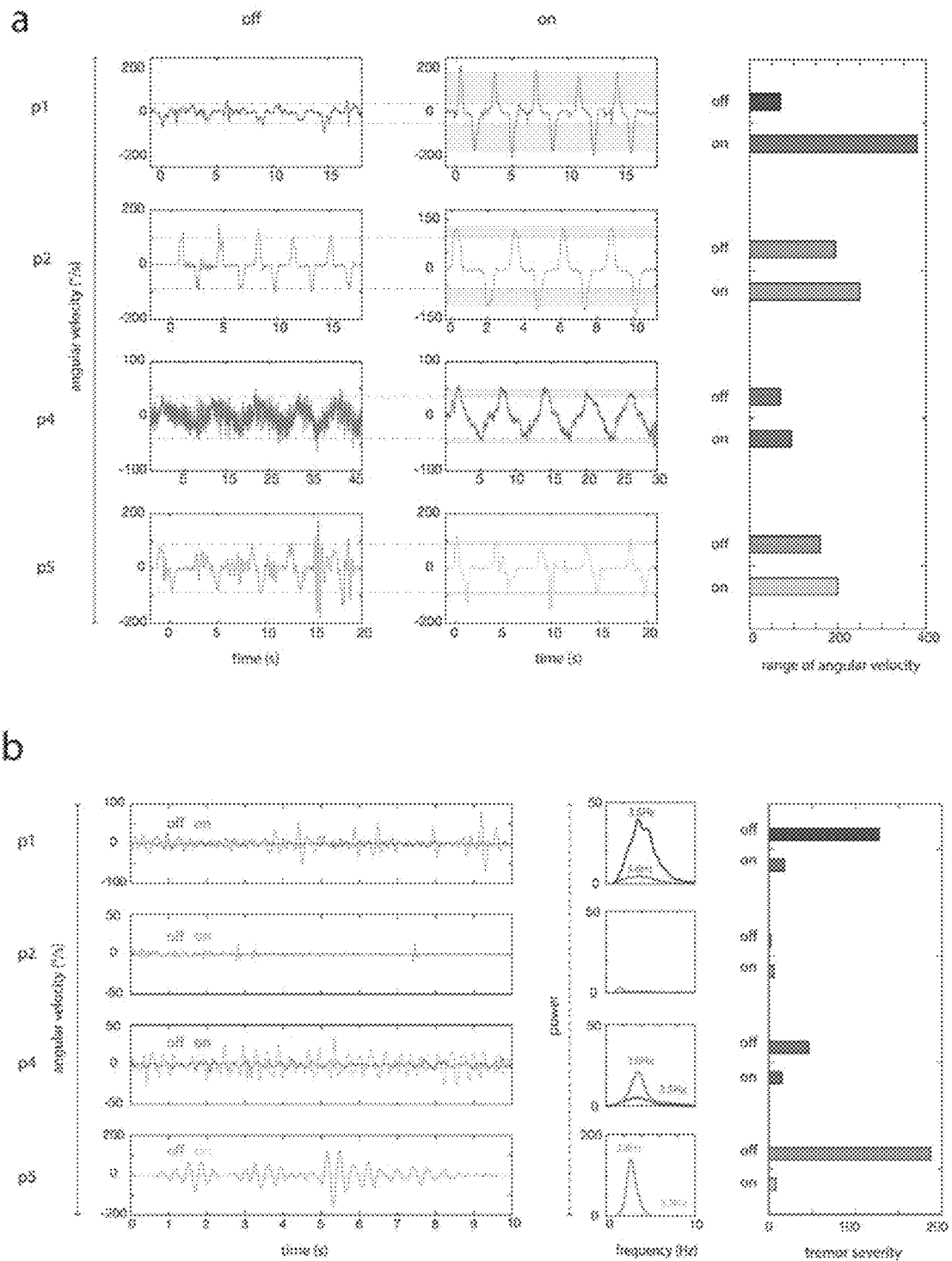

FIG. 8A-B are graphs of the angular velocity and tremor severity at STIM-ON and STIM-OFF from electromyogram data gathered in the example study, for four patients P1, P2, P4 and P5. In FIG. 8, angular velocity of motion in the joint of each patient is plotted against time in both the STIM-OFF and STIM-ON state. The right hand plot in FIG. 8A shows the range of angular velocity in STIM-OFF and STIM-ON states for each patient. The right hand plot in FIG. 8B shows a significant reduction in tremor severity during STIM-ON for the patients exhibiting the most severe tremor symptoms.

Discussion

This example study demonstrates that combined STN/VIM DBS is an effective and safe stimulation technique for severe tonic-painful and tremulous cervical dystonia. Combined stimulation of two brain targets significantly improves motor symptoms, non-motor symptoms (pain, sleep and psychiatric symptoms), disability and quality of life.

Time course of improvement was rapid, occurring since the time of first programming session, as opposed to pallidal stimulation whose benefits especially on tonic posturing may appear week to months later. The acute effect of stimulation was still present at 12 months follow-up, as demonstrated by clinical, EMG and kinematic data. The

TABLE 2

| Subject number | LEFT ELECTRODE | RIGHT ELECTRODE | mA (LEFT) | mA (RIGHT) | mcs (LEFT) | mcs (RIGHT) | Hz (LEFT) | Hz (RIGHT) |
|---|---|---|---|---|---|---|---|---|
| 1 | 3-(60%), 7-(40%), case + | 2-, case + | 2.4 | 1.2 | 60 | 50 | 130 | 130 |
| 2 | 2-(60%), 3-(40%), case + | 2-(50%), 4-(50%), case + | 2.9 | 1 | 60 | 60 | 130 | 130 |
| 3 | 4-(20%), 5-(70%), 6-(10%), case + | 3-(50%), 5-(50%), case + | 3.4 | 3.7 | 40 | 60 | 130 | 130 |
| 4 | 6-(30%), 7-(70%), case + | 7-(100%) case + | 1.1 | 2.6 | 30 | 50 | 130 | 130 |
| 5 | 3-(40%), 6-(60%), case + | 3-(50%), 5-(50%), case + | 3.8 | 3.5 | 90 | 60 | 130 | 130 |
| 6 | 3-(100%), case + | 4-(100%), case + | 3.3 | 3.4 | 60 | 60 | 130 | 130 |
| 7 | 6-(30%), 7-(60%), 8-(10%), case + | 5-(60%), 6-(40%), case + | 4 | 3.5 | 60 | 80 | 130 | 130 |
| 8 | 6-(40%), 7-(60%), case + | 5-(100%), case + | 1.5 | 1.8 | 60 | 60 | 130 | 130 |

Side Effects

Post-surgical side effects were dysphonia (N=1, duration =5 days), surgical wound erythema at site of IPG implant (N=1).

During the first programming sessions, the following side effects were recorded: upper limb chorea (N=2), increased pain for worsening of tonic posture of the head (N=1 at 2.0 mA with a bilateral STN stimulation); tonic deviation of face muscles (N=1), dizziness (N=1 with thalamic stimulation), paraesthesia (N=1 with STN, N=1 with VIM), light-headedness (N=1 with VIM stimulation). All these side effects were transitory and remitted after stimulation parameters adjustment. No significant speech of gait problem was registered.

Chronic side effects from stimulation were: minimal difficulty in word articulation (n=1), hand paraesthesia (n=1).

Neuroimaging Data

FIG. 7 shows electrode positions and aggregated volumes of tissue activation (orange) by patient in relation to STN (green), VIM (pink) and red nuclei in the coronal plane, anterior foremost of the patient's T-2 weighted MRI.

immediate symptomatic improvement enables the neurologist to directly target motor and non-motor aspects, rather than be guided only by the threshold for side-effects. Both dystonic postures and tremor were ameliorated by combined STN/VIM-VoP DBS or combined VIM-VoP/Zi stimulation.

The data in this example study demonstrate that STN and VIM stimulation contributes to ameliorate dystonic postures and dystonic tremor of the head in CD with a low rate of side effects. Dual targeting of ventrolateral thalamus and STN by an octopolar electrode lead allows stimulation in addition to VIM/VoP others targets such as the STN or ZI. Stimulation of the ventrolateral thalamus (VIM/VoP) was able not only to improve tremor, but also pain, dystonic head posturing and head range of motion.

The data show that combined STN/VIM DBS is effective for treatment of motor and non-motor symptoms of refractory and disabling tonic-painful and tremulous cervical dystonia.

CONCLUSION

Aspects of the present disclosure have been described with particular reference to the examples illustrated. While specific examples are shown in the drawings and are herein described in detail, it should be understood, however, that the drawings and detailed description are not intended to limit the invention to the particular form disclosed. It will be appreciated that variations and modifications may be made to the examples described within the scope of the present invention, as defined by the claims.

The invention claimed is:

1. A deep brain stimulation method for use in the treatment of cervical dystonia, comprising
   inserting a stimulation device into the brain of a patient, the stimulation device being configured to provide electrical stimulation to affect first and second stimulation targets within the brain;
   the first stimulation target being the subthalamic nucleus (STN); and
   the second stimulation target being either
   the ventralis oralis posterior thalamus (VOP), or
   both the ventral intermediate nucleus (VIM) and the ventralis oralis posterior thalamus (VOP),
   wherein the stimulation device is inserted on a posterior frontal extraventricular trajectory going through premotor cortex.

2. The method of claim 1, further comprising controlling the stimulation device to activate the first stimulation target and the second stimulation target simultaneously.

3. The method of claim 1, comprising transmitting electrical pulses generated by a pulse generator through an electrode lead to one or more electrical contacts of the stimulation device.

4. The method of claim 3, comprising providing an electrical stimulation using a single electrical contact of the electrode lead to affect both the first stimulation target and the second stimulation target.

5. The method of claim 3, comprising providing electrical stimulations using a first electrical contact of the electrode lead to affect the first stimulation target and a second electrical contact of the electrode lead to affect the second stimulation target.

6. The method of claim 5, wherein the first electrical contact contacts the first stimulation target and the second electrical contact contacts the second stimulation target during the electrical stimulations.

7. The method of claim 5, comprising applying electrical stimulation defined by first stimulation parameters to the first electrical contact and applying electrical stimulation defined by second stimulation parameters to the second electrical contact, wherein the first and second stimulation parameters are identical to each other for each of one or more of the following: frequency, pulse width and current.

8. The method of claim 3, wherein the electrode lead comprises eight electrical contacts disposed at separate locations on the electrode lead.

9. The method of claim 3, wherein the one or more electrical contacts are disposed to span between 9 mm and 20 mm in a longitudinal direction of the electrode lead.

10. The method of claim 3, wherein the one or more electrical contacts comprises a plurality of electrical contacts each having a length (L) of between 0.9 mm and 2 mm and being spaced between 0.2 mm and 2 mm apart along the electrode lead.

11. The method of claim 3, wherein each of the one or more electrical contacts continuously surrounds an axis of the electrode lead.

12. The method of claim 1, comprising applying electrical stimulation at a frequency greater than or equal to 60 Hz and less than or equal to 255 Hz frequency and a pulse width greater than or equal to 20 μs and less than or equal to 450 μs.

13. The method of claim 1, wherein the stimulation device is configured to affect a third stimulation target in the brain, the third stimulation target being the Zona Incerta (ZI).

14. The method of claim 1, wherein the method is for the treatment of cervical dystonia.

15. The method of claim 14, wherein the method is for the treatment of tonic cervical dystonia.

16. The method of claim 14, wherein the method is for the treatment of non-motor symptoms of cervical dystonia.

17. The method of claim 1, comprising inserting the stimulation device into a first hemisphere of the brain and a second hemisphere of the brain, wherein the stimulation device is configured to provide electrical stimulation to affect both hemispheres of the brain of the patient.

* * * * *